(12) United States Patent
Pourmand et al.

(10) Patent No.: US 9,187,782 B2
(45) Date of Patent: Nov. 17, 2015

(54) DNA TEMPLATE TAILORING USING PNA AND MODIFIED NUCLEOTIDES

(75) Inventors: Nader Pourmand, Scotts Valley, CA (US); Muhammad Akram Tariq, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 742 days.

(21) Appl. No.: 13/027,926

(22) Filed: Feb. 15, 2011

(65) Prior Publication Data

US 2011/0207118 A1 Aug. 25, 2011

Related U.S. Application Data

(60) Provisional application No. 61/306,474, filed on Feb. 20, 2010.

(51) Int. Cl.
*C12Q 1/68* (2006.01)
(52) U.S. Cl.
CPC .................. *C12Q 1/6869* (2013.01)
(58) Field of Classification Search
None
See application file for complete search history.

(56) References Cited

U.S. PATENT DOCUMENTS

| | | |
|---|---|---|
| 6,531,282 B1 | 3/2003 | Dau et al. |
| 2005/0112569 A1 | 5/2005 | Chung et al. |

FOREIGN PATENT DOCUMENTS

WO 98/13523 A1 4/1998

OTHER PUBLICATIONS

Beau-Faller et al. (Br J Cancer, 2009, vol. 100, p. 985-992).*
Vallone et al. (Int J Legal Med, 2004, 118:147-157).*
Styman et al. (International Congress Series, 2006, vol. 1288:669-671).*
Liu et al. (Biotechniques, 2004, 36:156-166).*
Demers et al. (Nucleic Acids Research, 1995, 23(15)3050-3055).*
Caetano-Anolles, et al., "Buffer Components Tailor DNA Amplification with Arbitrary Primers", Genome Research, 1994 4: 59-61.
Chou, et al., "Unlabeled oligonucleotide probes modified with locked nucleic acids for improved mismatch discrimination in genotyping by melting analysis", BioTechniques 39:644-650 (Nov. 2005).

* cited by examiner

*Primary Examiner* — Stephanie K Mummert
(74) *Attorney, Agent, or Firm* — David J. Aston; Bozicevic, Field & Francis LLP

(57) ABSTRACT

Disclosed is a method whereby a repetitive nucleic acid sequence, such as a short tandem repeat (STR), may be characterized as to its length. Pyrosequencing is used to sequence an STR repetitive region to measure the length of STRs in a rapid manner. A combinatorial approach is disclosed for the addition of multiple nucleotides (e.g., two mononucleotides) at a time by the polymerase, which reduces the sample analysis time by half. In addition, modified nucleic acids, such as peptide nucleic acids, are used as blocking probe to stop polymerization on the flanking region which makes it possible to use pyrosequencing for DNA length measurement both in the case of homozygous or heterozygous samples for varying repeat patterns of different markers. Further, dideoxynucleotides are added to stop polymerization in the flanking region of the STR.

12 Claims, 10 Drawing Sheets

A: SEQ ID NO: 17
B: SEQ ID NO: 18

Fig. 2A

A: SEQ ID NO: 21
B: SEQ ID NO: 22

A: SEQ ID NO: 20

B: SEQ ID NO: 23

DNA TEMPLATE TAILORING USING PNA AND MODIFIED NUCLEOTIDES

CROSS-REFERENCE TO RELATED APPLICATIONS

This application claims priority from U.S. Provisional Patent Application No. 61/306,474, filed on Feb. 20, 2010, which is hereby incorporated by reference in its entirety.

STATEMENT OF GOVERNMENTAL SUPPORT

This invention was made with U.S. Government support under National Institutes of Health Grant No. P01-HG000205 and National Science Foundation Grant DBI 0830141. The U.S. Government has certain rights in this invention.

REFERENCE TO SEQUENCE LISTING, COMPUTER PROGRAM, OR COMPACT DISK

Applicants assert that the text copy of the Sequence Listing is identical to the Sequence Listing in computer readable form found on the accompanying computer file named 482__26__1_seq_ST25.txt, created Feb. 14, 2011, 8 KB. Applicants incorporate the contents of the sequence listing by reference in its entirety.

BACKGROUND OF THE INVENTION

1. Field of the Invention

The present invention relates to the fields of genetic analysis, DNA sequencing, and further is generally directed to the detection of short tandem repeat (STR) genetic markers in a genomic system.

2. Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Measurement of the length of DNA fragments plays a pivotal role in genetic mapping, disease diagnostics, paternity testing and human identification. Traditionally, capillary electrophoresis is used for DNA length measurement and genotyping of short tandem repeats. This requires labeled primers and allelic ladders as standards to avoid typical run-to-run or instrument-to-instrument variations. However, the limiting factor with this sequencing approach in heterozygous sample analysis is unsynchronized polymerization in alleles with different lengths that can lead to imbalanced heterozygote peak height ratios.

DNA sequencing has revolutionized the field of bioscience and its use has been critical for a number of important medical discoveries. Sequencing technologies have evolved over the years. One of the first, the Sanger method, has provided an elegant sequencing method widely used for the last three decades. A more recently developed technology, pyrosequencing, is an alternative method to Sanger's for sequencing of DNA fragments with a number of advantages. Pyrosequencing is based on sequencing by synthesis method that monitors the polymerase activity coupled to 2-enzymes to generate a detectable light response; i) ATP-Sulfurylase converts inorganic pyrophosphate (PPi) to ATP generated by polymerase during nucleotide incorporation, and ii) luciferase that uses ATP as a source of energy to generate light.

The present invention is described as using pyrosequencing, but other suitable sequencing-by-synthesis platforms can be used. Commercial sequencing by synthesis platforms are available, such as the Genome Sequencer from Roche/454 Life Sciences, the Genome Analyzer from Illumina/Solexa, the SOLiD system from Applied BioSystems, Pacific Biosystem and the Heliscope system from Helicos Biosciences. In some embodiments, the sequencing platforms used in the methods of the present invention have one or more of the following features: 1) four differently optically labeled nucleotides are utilized (e.g., Genome Analyzer); 2) sequencing-by-ligation is utilized (e.g., SOLiD); 3) pyrosequencing is utilized (e.g., Roche/454); and 4) four identically optically labeled nucleotides are utilized (e.g., Helicos).

Since STRs can comprise in the range of from 2-7 bases repeated 5-30 times, it is preferred to use a sequencing method that has a read length that can extend up to about 150 bases. For analyzing sequences longer than the read length of the sequencing by synthesis method used, computer-aided methods exist for assembling overlapping fragments of sequence; one simply is required to carry deeper sequencing.

Sequencing technologies have become even more important recently with interests of many groups to conduct whole genome sequencing both for comparisons of different species, as well as different humans and has become the foundation of personalized medicine. One of the critical issues in DNA sequencing of whole genomes is the problem of relatively short lengths of DNA reads using most approaches, including Sanger's. Short read lengths complicate the informatics needed to analyze and place those sequences in the context of the whole genome. Currently, DNA length determinations of short tandem repeats (STRs) for forensic DNA analysis and detection of mutated genes for clinical applications are performed using polymerase chain reaction (PCR) fragment size measurements. This approach is based on an electrophoretic technique. It involves use of dye labeled primers, requires very careful data analysis and is limited by the occurrence of technology artifacts.

Pyrosequencing technology has also been used in a broad range of applications such as genotyping of microbes, SNP genotyping, mutation detection and gene identifications. This technique has the potential to provide a robust method for DNA length measurement which is time and cost competitive compared to other approaches. It is automatable and provides easily interpretable results. In pyrosequencing, there is no need for specific dye labeling of PCR products. The technique is also helpful and has been shown to be capable of determining the sequence variants within or near repeat regions in short tandem repeats (STRs) in addition to fragment length differences. This is particularly useful in avoiding confusion during interpretation of results for human identity testing or relationship testing.

STRs are short, tandemly repeated DNA sequences which are interspersed throughout the human genome at up to several hundred thousand loci. They are also found in animals and plants where they are similarly useful as genetic markers. STRs are typically 2-7 base pairs in length repeated 5-30 times. These loci are highly polymorphic with respect to the number of repeat units they contain and may vary in internal structure as well. Variation in the number of STR repeat units at a particular locus causes the length of the DNA at that locus to vary from allele to allele and from individual to individual. Thus, many allelic variants exist within the human population, and STRs provide a rich source of genetic markers.

Characterization of the alleles at specific STR loci for purposes of individual identification usually begins with their PCR amplification from genomic DNA of the individual whose genome contains those loci. Although a particular repeat unit may be common to several different STR loci, identification of a particular STR locus may be effected via PCR amplification by utilizing primer pairs which hybridize to unique DNA sequences which flank the repeat region, i.e., unique sequences located 5' and 3' to the repeat units. Use of such unique primers makes it possible to simultaneously amplify many different STR loci in a single DNA sample, a technique referred to as multiplexing. The resulting PCR products (amplicons) from the various loci may then be separated by electrophoresis and identified by determining their lengths in comparison to known DNA standards.

Common repeats used for typing and linkage analysis are "CA" "GATA" or "ACTT" sequences. That is, an STR may contain a given number of repeats of sequences containing CA, ACTT, or the like. Exemplified below are repeats of AGAT found in two human STRs. The analysis of individual humans or other organisms is based on how many repeats they have. They may be homozygous, or heterozygous, i.e., have one number of repeats on one chromosome in a pair and another number on the other chromosome in the pair, as explained further below.

Specifically designed as amplification-based detection methods, STR and microsatellite-based DNA typing offer some practical advantages over typing methods based on larger repeat sequences. For example, PCR amplification using primers targeted to a specific STR sequence typically generates 50-to-500-bp-sized fragments without compromising allelic diversity. This allows for easier sizing of a wider range of alleles on a single electrophoretic separation, as compared with larger tandem repeat sequences that typically produce an order-of-magnitude greater range in fragment size diversity Specific Patents and Publications U.S. Pat. No. 6,531,282 to Dau, et al., issued Mar. 11, 2003, entitled "Multiplex amplification and analysis of selected STR loci," discloses means to identify the alleles present in a DNA-containing sample by providing subsets of loci for amplification by multiplex PCR. The loci include the thirteen CODIS short tandem repeat (STR) loci and amelogenin. The loci within each subset are grouped so that, upon PCR amplification, the amplicons produced within a given subset do not overlap.

U.S. 2005/0112569 A1 by Chung et al., entitled "Method of determining blood-relationship by typing STR alleles on the X chromosome and DNA typing kit using the SA," published May 26, 2005, discloses STR alleles including GATA172D05.

BRIEF SUMMARY OF THE INVENTION

The following brief summary is not intended to include all features and aspects of the present invention, nor does it imply that the invention must include all features and aspects discussed in this summary.

Described below is a rapid DNA length measurement method using peptide nucleic acids (PNAs) and/or dideoxy dNTPs to tailor DNA templates for sequencing. The method may use a combinatorial pyrosequencing strategy, which may be used as a faster, more accurate alternative to de novo sequencing. The available data suggests that the method is a reliable, rapid, information-rich and cost-effective approach for DNA length measurements for genotyping of STRs. The combinatorial pyrosequencing interrogates two bases at a time by allowing the polymerase to incorporate two nucleotides to DNA template which reduces by half the analysis time. In addition, the invention enables genetic analysis of predetermined, discrete segments of DNA, where the segment begins at a polymerase start primer and ends at a blocking probe. Examples show the effect of PNA as a blocking probe to stop polymerization and further show the analysis of heterozygous samples (i.e. where the segments are of different lengths) by sequencing. Thus the method comprises a step of extending the polymerization primer 5' to 3' by using said polymerase enzyme, said extending stopping at 5' end of the modified oligonucleotide. The extending stops exactly when the blocking probe is reached, or in the vicinity of the blocking probe, depending on experimental conditions, and the use of the modified nucleotide, described below. Overall, the process may be described as follows:

The present method is useful for characterizing a sample nucleic acid sequence by length, such as the length of a given STR at a given locus in a certain chromosome. The nucleic acid sequence to be analyzed will have, outside the STR region, a 5' flanking region and a 3' flanking region. One can carry out the following steps:

(a) hybridizing a polymerization primer to said 3' flanking region of the sample sequence; the polymerization primer serves to prime a polymerization reaction on the strand, which polymerization can be used to obtain sequence information.

(b) hybridizing a modified oligonucleotide to said 5' flanking region of the sample sequence, said modified oligonucleotide resistant to displacement by a polymerase enzyme; this will block polymerization, so that the end of a sequence read is indicative of length of the nucleic acid sequence being analyzed.

(c) extending the polymerization primer 5' to 3' by using said polymerase enzyme, said extending stopping at 5' end of the modified oligonucleotide; and (d) said extending comprising the step of adding nucleotides complementary to the sample sequence and a dideoxy nucleotide complementary to a nucleotide in the 5' flanking region. As described below, the dideoxy nucleotide also blocks further polymerization, and is chosen to not be incorporated into the repetitive sequence. For example, if the repetitive sequence consists of As and Ts, the dideoxy nucleotide will be a C or G, that will be incorporated after the STR region has been polymerized.

This approach provides a new platform for rapid and cost affective DNA length measurement for STRs and resequencing of small DNA fragments such as mitochondrial DNA control regions. The use of the dideoxy nucleotide is based on the fact that it carries no phosphate group for further polymerization. Other chain-terminating nucleotides could be used. The present method may be used on genomic samples which are diploid so that two copies of a region to be analyzed exits, and the present method may be used to distinguish heterozygous markers.

BRIEF DESCRIPTION OF THE DRAWINGS

FIG. 1A): When there is no DNA template tailoring, it is not possible to interpret the sequence results due to the occurrence of unsynchronized polymerization of heterozygous individuals at this locus, FIG. 1B): DNA Template tailoring using ddNTP can't produce accurate genotypes showing extra repeat. FIG. 1C): However, DNA template tailoring using PNA along with terminating nucleotides (ddNTP) results in accurate determination of genotype by combinatorial pyrosequencing.

FIG. 2A): Template tailoring of homozygous samples using PNA (genotype 6, 6),

FIG. 3A): Template tailoring of homozygous samples using PNA as well as ddCTP. Note that the PNA probe has a 4 bp complementary to the repeat region. Therefore, the genotype for this homozygous sample was considered 7, 7 instead of the apparent genotype 6, 6 for this sample. FIG. 3B): Template tailoring of heterozygous samples using PNA as well as ddCTP. Note that the PNA probe has 4 bp complementary to the repeat region. Therefore, the genotype for this heterozygous sample was considered 7, 12 instead of the apparent genotype 6, 11 for this sample.

DETAILED DESCRIPTION OF THE PREFERRED EMBODIMENT

Overview

Figure 1:
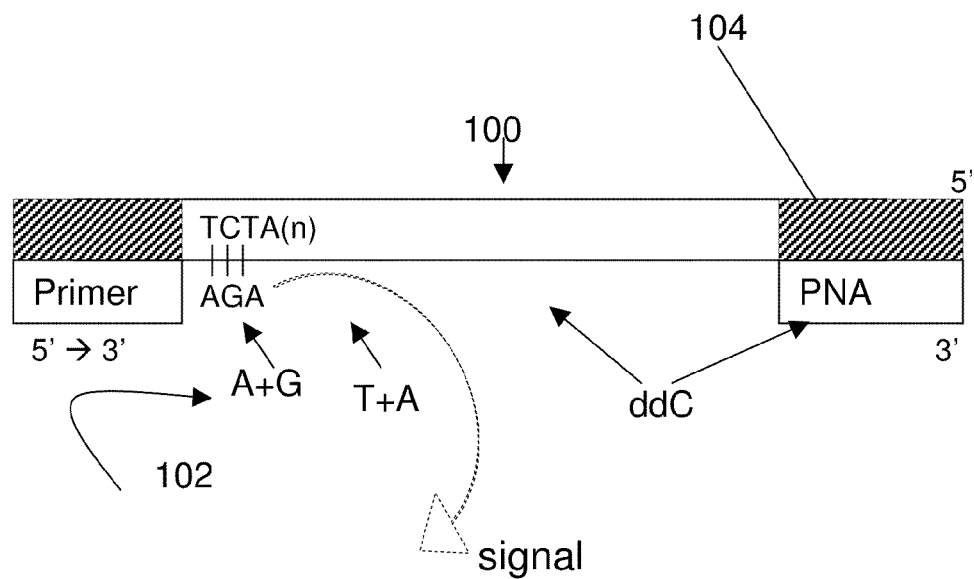
FIG. 1 shows the concept of DNA template tailoring: In this figure, one chromosome is shown; for autosomal markers, and X markers in females, there will be two chromosomes being analyzed. The polynucleic acid being analyzed 100 (e.g. an STR region) is hybridized to a primer at the 3' end of the sequence, so that the primer can be extended by a polymerase in the 5' to 3' direction, as is known. The primer has a sequence complementary to a known flanking region of the region being analyzed. The extension incorporates nucleotides complementary to the polynucleic acid to be analyzed. These are shown in the figure as A, G and A. They are incorporated through the addition of mononucleotides indicated as "sequencing bases" 102. The sequencing bases are being added two at a time; the particular two base units to be used are chosen on the basis of the repetitive sequence being analyzed. That is, a known STR will have a known pattern of bases, here, AGAT, which is repeated many times. When a complementary base is incorporated, a signal is produced. The preferred signal is generated by pyrosequencing, which enzymatically detects the pyrophosphate released from the incorporation of the sequencing bases. Other sequencing methods may be used. At the same time, a chain terminating nucleotide that is not complementary to the STR is added, in this case dideoxycytosine, ddC. It will not be incorporated until it encounters a complementary base, i.e., a G, which will not happen until after the polymerization reaction extends past the STR region, unless there is a mutation in the STR. ddC prevents further chain extension. At the 5' region of the polynucleic acid to be analyzed, shown in FIG. 1 at 104, a modified oligonucleotide, indicated as "PNA," or peptide nucleic acid is hybridized to a portion of the polynucleic acid strand being analyzed that is at or near the 5' end, of the region, as shown in the figure; this will block the polymerization reaction and result in the sequence length obtained from incorporating the bases by the polymerase being indicative of the STR region's length.

The present method uses sequencing by synthesis, exemplified by pyrosequencing, to measure the length of STRs in a rapid manner. This method employs existing pyrosequencing technology with several improvements. First, we used a combinatorial approach for the addition of two nucleotides at a time by the polymerase which reduces the sample analysis time by half. Second, we used PNA as blocking probe to stop polymerization on the flanking region which made it possible that pyrosequencing can be used for DNA length measurement both in the case of homozygous or heterozygous samples for varying repeat patterns of different markers.

The present methods could be readily used for forensic DNA testing. The Federal Bureau of Investigation (FBI) uses a standard set of 13 specific STR regions for Combined DNA Index System (CODIS). CODIS is a software program that operates local, state, and national databases of DNA profiles from convicted offenders, unsolved crime scene evidence, and missing persons. The odds that two individuals will have the same 13-loci DNA profile is about one in a billion.

Pyrosequencing as employed here has certain advantages over traditional methods of DNA length measurement such as by capillary electrophoresis. First, there is no need for specific dye labeling of the PCR product in pyrosequencing. Second, there is no discrepancy of DNA length measured by pyrosequencing due to errors between run-to-run or machine-to-machine such as found in capillary electrophoresis. Therefore, it eliminates the need of allelic ladders. Allelic ladders consist of all alleles found in a population for that marker and are used as a standard to measure the length of that particular STR to eradicate inaccuracies due to machine error.

During STR analysis, the PNA concentration with respect to the concentration of the PCR product is a critical parameter. The primer and PNA washing after the annealing step helped us to get reliable results. Otherwise, DNA polymerase shows stacking behavior due to free PNA which is not annealed and starts adding bases of repeats continuously which can cause confusion in interpreting the results. This method can also be used for other applications that use STR analysis such as evolutionary studies, linkage analysis for genetic diseases and cancer diagnostics. The multiplex pyrosequencing would further reduce the cost and analysis time for STR length measurement.

DEFINITIONS

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "modified oligonucleotide" is used herein to refer to a molecule having nucleic acid-like properties of specific base sequence recognition (e.g., base-pairing) and binding to a complementary strand, but having chemical modifications resulting in stronger binding to the target strand. The function, as explained here, is to block further processing of a polymerase, such as the Klenow fragment of DNA polymerase. The exemplified modified oligonucleotides are peptide nucleic acids.

The term "PNA" is used herein to refer to a peptide nucleic acid. PNAs are nucleic acid analogs in which the sugar phosphate backbone of natural nucleic acid has been replaced by a synthetic peptide backbone, usually formed from N-(2-amino-ethyl)-glycine units, resulting in an achiral and uncharged mimic. PNAs are described further in Ray et al., "Peptide nucleic acid (PNA): its medical and biotechnical applications and promise for the future," The *FASEB Journal*, 2000; 14:1041-1060. As described there, the backbone of PNA carries 2-aminoethyl glycine linkages in place of the regular phosphodiester backbone of DNA, and the nucleotide bases are connected to this backbone at the amino nitrogens through a methylene carbonyl linker. Being achiral, peptide nucleic acids can be synthesized without need of any stereo-selective pathway. PNA oligomers can be prepared following standard solid-phase synthesis protocols for peptides.

The term "pyrosequencing" refers to a method based on the detection of the pyrophosphate group that is generated when a nucleotide is incorporated in a DNA polymerase reaction. Each of the four deoxynucleotides (dNTPs) is added sequentially to the DNA template to be sequenced with a cocktail of enzymes and substrates in addition to the usual polymerase reaction components. If the added nucleotide is complementary with the first available base on the template, the nucleotide will be incorporated and a pyrophosphate will be released. The released pyrophosphate is converted to ATP by sulfurylase, and this ATP is the substrate for a luciferase, e.g., firefly luciferase, which reaction produces visible light. If the added nucleotide is not incorporated, no light will be produced and the nucleotide will simply be degraded by the enzyme apyrase. Details on carrying out pyrosequencing may be found, e.g., at Ronaghi M., Uhlen M, Nyren P. A sequencing method based on real-time pyrophosphate. *Science,* 281 (5375), 363-365 (1998).

The term "repetitive sequence" means a polynucleic acid sequence characterized by repeating sequences of bases, e.g., 2-20 repeats of sequences of 2-10 bases. These include STRs, microsatellites, VNTRs and other tandem repeats. Characterizing by length means that a repetitive sequence can be measured so that the number of repeats in a repetitive sequence at a given locus is known. For example, it could be determined that a given STR locus (TPOX, sequence AATG) could be characterized as having 13 full four base repeats plus 2.

The term "STR" means short tandem repeats; the term is explained in detail below. STRs are short sequences of DNA, normally of length 2-5 base pairs, that are repeated numerous times in a head-tail manner, i.e. the 16 bp sequence of "gatagatagatagata" would represent 4 head-tail copies of the tetramer "gata". The polymorphisms in STRs are due to the different number of copies of the repeat element that can occur in a population of individuals.

The term "VNTR" means variable number of tandem repeats." One VNTR in humans is a 17 bp sequence of DNA repeated between 70 and 450 times in the genome. The total number of base pairs at this locus could vary from 1190 to 7650.

The term "microsatellite" means repeating sequences of 1-6 base pairs of DNA. A typical microsatellite is a (CA)n repeat, where n is variable between alleles. These markers often present high levels of inter- and intra-specific polymorphism, particularly when tandem repeats number ten or greater. The repeated sequence is often simple, consisting of two, three or four nucleotides (di-, tri-, and tetranucleotide repeats respectively), and can be repeated 10 to 100 times. CA nucleotide repeats are very frequent in human and other genomes, and are present every few thousand base pairs.

The term "tandem repeat" is intended to cover STRs, microsatellites, and other regions of regularly repeating units of DNA, where analysis of length is desired.

General Methods and Materials

The fragment length of a particular STR for a homozygous individual can be determined by using pyrosequencing. However, measurement of STR length for a heterozygous individual has been a challenge. Here, we demonstrated proof of principle for DNA template tailoring by devising combinatorial pyrosequencing to analyze DNA lengths.

Critical to this new approach are modified oligonucleotides which block polymerase processing and additional base incorporation. Exemplified here are peptide nucleic acid (PNA) probes designed to hybridize to a flanking region to block the ability of polymerase to incorporate dNTP to a growing DNA strand. PNA is a nucleobase oligomer in which the entire backbone has been replaced by N-(2-aminoethyl) glycine units. PNA is able to recognize specific sequences of DNA, obey the Watson-Crick hydrogen bonding scheme, and the hybrid complexes exhibit extraordinary thermal stability and unique ionic strength effects. PNA has been previously reported to be capable of inhibiting transcription as well as translation.

The modified oligonucleotide will be chosen with the strand displacement activity of the polymerase in mind. One may use a DNA Polymerase I, Large (Klenow) Fragment is a proteolytic product of *E. coli* DNA Polymerase I which retains polymerization and 3'→5' exonuclease activity, but has lost 5'→3' exonuclease activity. Klenow retains the polymerization fidelity of the holoenzyme without degrading 5' termini. It is known that the Klenow fragment can be blocked with a triple helix. For use of this approach, see Haccia et al., "Inhibition of Klenow fragment DNA polymerase on double-helical templates by oligonucleotide-directed triple-helix formation," *Biochemistry,* 1994 May 24; 33(20):6192-200. Antibodies may also be used to block polymerase activity. RNA may also be used. See, Horton et al., "Strategic down-regulation of DNA polymerase β by antisense RNA sensitizes mammalian cells to specific DNA damaging agents," *Nucleic Acids Research,* 1995, Vol. 23, No. 19 3810-3815. Oligonucleotides may be prepared with modified bases, such as base methylation. Polymerases such as T4 DNA polymerase, which does not have strand displacement activity, can be used.

As described here, PNA can be employed to tailor DNA length for polymerization. In combinatorial pyrosequencing, two nucleotides are dispensed at once to allow hybridization to two bases at a time. The interrogation of two nucleotides at a time reduces the sequencing time to half. This allows for real time DNA length measurements in the case of both homozygous and heterozygous samples. Combinatorial pyrosequencing approach was used to analyze two STRs (GATA172D05 & GATA31E08) in 15 human DNA samples. The available data suggest that the method described here is a reliable, rapid, information-rich and cost-effective approach for DNA length measurements and may be useful for genotyping STRs for both forensic and clinical applications.

The examples below provide proof of principle that the length of DNA can be measured using combinatorial Pyrosequencing. The basis of the technology is the use of PNA as a blocking probe to stop polymerization on flanking regions for heterozygous samples. The strategy to determine DNA length is depicted in FIG. 1.

The methods described here can be applied to a variety of nucleic acids sequences where length is to be determined. These typically will contain a number of predetermined repetitive sequences. Further information on the STRs described here, as well as other STRs may be found, for example, online at ChrX-STR.org 2.0, http(colon slash slash)xdb.qualitype. de/xdb/index.jsf; jsessionid=11AD54200516CD6A0F7CCA2282179537, or at http(colon slash slash)www.med.uni-magdeburg.de/chrx/idio_gramm.

Marker GATA172D05 is described there as follows:
Cytogenetic localization: q 23.00
Physical localization NCBI 36: 113.061
Genetic localization deCODE: 110.42
Rutgers Map v.2: 124.36
Primer PrimerF: 5'-TAGTGGTGATGGTTGCACAG-3' (SEQ ID NO: 1)

PrimerR: 5'-ATAATTGAAAGCCCGGATTC-3' (SEQ ID NO: 2)

Typical structure

| Allele | bps | Sequence composition |
|---|---|---|
| 5-12 | 104-132 | PF-N5-(TAGA)5-12 N39-PR |

Marker GATA31E08
Cytogenetic localization: q 27.10
Physical localization NCBI 36: 140.062
Rutgers Map v.2: 160.54

PrimerF: 5'-AGGGGAGAAGGCTAGAATGA-3' (SEQ ID NO: 3)

PrimerR: 5'-CAGCTGACAGAGCACAGAGA-3' (SEQ ID NO: 4)

Typical structure

| Allele | bps | Sequence composition |
|---|---|---|
| 8 | — | -(AGAT)8- |
| 9 | — | -(AGAT)9- |
| 11 | — | -(AGAT)11- |
| 12 | — | -(AGAT)12- |

Marker HPRTB
LOCUS HUMHPRTB Intron 3, Human hypoxanthine phosphoribosyltransferase (HPRT) gene (SEQ ID NO: 24)
Primer F: 5' TCTCTATTTCCATCTCTGTCTCC-3'

(SEQ ID NO: 25)
Primer R: 5' TCACCCCTGTCTATGGTCTCG-3'

Regular alleles: 9-17
Length (bp): 144-176
Sequence Composition: PF $N_{30}$ $(TCTA)_n$ $N_{34}$ PR Any tandem repeating region may be used in the present method. In particular, it is contemplated to use core STR loci for inclusion within the national database known as CODIS (Combined DNA Index System). The 13 CODIS loci are CSF1PO, FGA, TH01, TPOX, VWA, D3S1358, D5S818, D7S820, D8S1179, D13S317, D16S539, D18S51 and D21S11. These loci are nationally and internationally recognized as the standard for human identification. A list of STR loci, including the core CODIS loci, can be found at http (colon slash slash) www.cstl.nist.gov/strbase/str_fact. Table 2 describes the 13 CODIS loci.

TABLE 2

CODIS STR loci

| Name of the locus | Chromosomal location | Repeat | Primers | Observed alleles |
|---|---|---|---|---|
| CSF1PO | 5q33.1; human c-fms proto-oncogene for CSF-1 receptor gene, 6th intron Chr 5; 149.436 Mb | [AGAT] | 5'-AACCTGAGTCTGCCAAGGACTAGC-3' (AGAT strand) (SEQ ID NO: 26) 5'-TTCCACACACCACTGGCCATCTTC-3' (TCTA strand) (SEQ ID NO: 27) | 5-16 |
| FGA | 4q28; located in the third intron of the human alpha fibrinogen gene Chr 4; 155.866 Mb | complex tetra-nucleotide repeat; $[TTTC]_3TT$ $TTTCT[CTTT]_n$ $CTCC[TTCC]_2$ | 5'-GCCCCATAGGTTTTGAACTCA-3' (CTTT strand) (SEQ ID NO: 28) 5'-TGATTTGTCTGTAATTGCCAGC-3' (GAAA strand) (SEQ ID NO: 29) | 12-51 |
| TH01 | 11p15.5; intron 1 of human tyrosine hydroxylase gene Chr 11; 2.149 Mb | [AATG] | 5'-GTGGGCTGAAAAGCTCCCGATTAT-3' (AATG strand) (SEQ ID NO: 30) 5'-ATTCAAAGGGTATCTGGGCTCTGG-3' (TCAT strand) (SEQ ID NO: 31) | 3-13 |
| TPOX | 2p25.3; intron 10 of human thyroid peroxidase gene Chr 2; 1.472 Mb | [AATG] | 5'-ACTGGCACAGAACAGGCACTTAGG-3' (AATG strand) (SEQ ID NO: 32) 5'-GGAGGAACTGGGAACCACACAGGT-3' (TTAC strand) (SEQ ID NO: 33) | 6-14 |

TABLE 2-continued

CODIS STR loci

| Name of the locus | Chromosomal location | Repeat | Primers | Observed alleles |
|---|---|---|---|---|
| VWA | 12p13.31; von Willebrand Factor, 40$^{th}$ intron Chr 12; 5.963 Mb | [AGAT] = bottom strand; with [TCTA] and [TCTG] and [TCCA] inserts | 5'-CCCTAGTGGATAAGAATAATC-3' (SEQ ID NO: 34) 5'-GGACAGATGATAAATACATAG GATGGATGG-3' (SEQ ID NO: 35) | 10-24 |
| D3S1358 | 3p21.31 Chr 3; 45.557 Mb | [AGAT], [TCTA] | 5'-ACT GCA GTC CAA TCT GGGT-3' (AGAT strand) (SEQ ID NO: 36) 5'-ATG AAA TCA ACA GAG GCT TG-3' (TCTA strand) (SEQ ID NO: 37) | 8-19 |
| D5S818 | 5q23.2 Chr 5; 123.139 Mb | [AGAT] | 5'-GGTGATTTTCCTCTTTGGTATCC-3' (SEQ ID NO: 38) 5'-[labelled]-AGCCACAGTTTACAACATTTGTATCT-3' (SEQ ID NO: 39) | 7-15 |
| D7S820 | 7q21.11 Chr 7; 83.433 Mb | [GATA] | 5'-[labelled]-ATGTTGGTCAGGCTGACTATG-3' (SEQ ID NO: 40) 5'-GATTCCACATTTATCCTCATTGAC-3' (SEQ ID NO: 41) | 6-14 |
| D8S1179 | 8q24.13 Chr 8; 125.976 Mb | [TATC] | 5'-TTTTTGTATTTCATGTGTACATTCG-3' (SEQ ID NO: 42) 5'-CGTAGCTATAATTAGTTCATTTTCA-3' (SEQ ID NO: 43) | 7-19 |
| D13S317 | 13q31.1 Chr 13; 81.620 Mb | [GATA] | 5'-ATTACAGAAGTCTGGGATGTG GAGGA-3' (SEQ ID NO: 44) 5'-[labelled]-GGCAGCCCAAAAAGACAGA-3' (SEQ ID NO: 45) | 7-15 |
| D16s539 | 16q24.1 Chr 16; 84.944 Mb | [GATA] | 5-GGGGGTCTAAGAGCTTGTAAAAAG-3' (SEQ ID NO: 46) 5'-[labelled]-GTTTGTGTGTGCATCTGTAAGCATGTATC-3' (SEQ ID NO: 47) | 5-15 |
| D18S51 | 18q21.33 Chr 18; 59.100 Mb | [GAAA] | 5'-CAA ACC CGA CTA CCA GCA AC-3' (GAAA strand) (SEQ ID NO: 48) 5'-GAG CCA TGT TCA TGC CAC TG-3' (SEQ ID NO: 49) | 8-27 |
| D21S11 | 21q21.1 Chr 21; 19.476 Mb | [TCTA], [TCTG] | 5'-GTG AGT CAA TTC CCC AAG-3' (SEQ ID NO: 50) 5'-GTT GTA TTA GTC AAT GTT CTC C-3' (SEQ ID NO: 51) | 24-41 |

EXAMPLES

Example 1

Probe and Primer Design and Synthesis

Oligonucleotides for amplification of the markers GATA172D05, GATA31E08 and HPRTB (Genbank accession no. M26434; 12 repeats) were designed by using primer3 software (http(colon slash slash) primer3.sourceforge.net) and were synthesized by IDT (Coralville, Iowa, USA). Either the forward or reverse primer was biotinylated. The sequences for oligonucleotides are shown in Table 2.

TABLE 2

The dye-labeling, sequences for amplification and sequencing oligonucleotides as well as PNA probes used for pyrosequencing.

| Marker | Dye Labeling* | SEQ ID NO: | Primer Sequences |
|---|---|---|---|
| Amplification primer-GATA172D05 | Biotin | 5<br>6 | 5'-Biotin/ataattgaaagcccggattc<br>5'-tagtggtgatggttgcacag |
| Seq. primer-GATA172D05 | No labeling | 7 | 5'-gtgatggttgcacagatata |
| PNA Probe GATA172D05 | No labeling | 8 | N-Terminus-gctatatcaatacct-C-Terminus |
| Amplification primer-GATA31E08 | Biotin | 9<br>10 | 5'-Biotin/cagctgacagagcacagaga<br>5'-aggggagaaggctagaatga |
| Seq. primer-GATA31E08 | No labeling | 11 | 5'-agatagatgatagggaggg |
| PNA Probe GATA31E08 | No labeling | 12 | N-Terminus-agataggagatacat-C-Terminus |
| Amplification primer-HPRTB | Biotin | 13<br>14 | 5'-Biotin/gtctctatttccatctctgtctcc<br>5'-ttctttctctcacccctgtct |
| Seq. primer-HPRTB | No labeling | 15 | 5'-gagaagggcatgaatttgctt |
| PNA Probe-HPRTB | No labeling | 16 | C-Terminus-gatagacagatagag-N-Terminus |

*Forward primer is always labeled

The fifteen bases sequence of the flanking region for each marker including GATA172D05, GATA31E08 and HPRTB were used to synthesize PNA probes in following manner.
1. GATA172D05: PNA sequence (N-terminus// - - - //C-terminus) of flanking region complementary to biotinylated strand of PCR product
2. GATA31E08: PNA sequence (N-terminus// - - - //C-terminus), 4-bp of repeat region and remaining 11 bp of flanking region complementary to biotinylated strand of PCR product
3. HPRTB: PNA sequence (C-terminus// - - - //N-terminus) of flanking region complementary to biotinylated strand of PCR product PNA was synthesized and HPLC purified by Biosynthesis Inc. (Lewisville, Tex., USA). PNA sequences are also shown in table 2.

Example 2

PCR Amplification and Sample Preparation

Fifteen blood samples were purchased from Stanford Blood Centre (Palo Alto, Calif., USA). Total Genomic DNA (gDNA) was extracted using Qiagen's QiaAMP DNA Blood Maxi Kit (www-dot-qiagen.com). Extractions were performed according to manufacturer's instructions. The quantity of DNA was determined by NanoDrop (Thermo Scientific, Wilmington, Del.) as per manufacturer's recommendation.

10 ng of gDNA was amplified in a single-plex PCR using biotin labeled primers in a 50 μl reaction volume containing; 10 ng of genomic DNA, 0.2 μM each forward and reverse primer for all three markers, 75 mM Tris HCl (pH 8.0), 2.0 mM MgCl$_2$, 200 μM of each dNTPs, 1.5 U of AmpliTaq Gold polymerase (Applied Biosystems, Foster City Calif., USA). The amplification was performed in a GeneAmp PCR System 9700 Thermal Cycler (Applied Biosystems, Foster City, Calif.) at the following conditions: 95° C. for 10 minutes, followed by 32 cycles of denaturing at 95° C. for 30 s, annealing at 57° C. for 20 s, extension at 72° C. for 12 s and a final extension at 72° C. for 7 min.

Capillary Electrophoresis: 1 μl of each PCR amplified product was added to 12 μl deionized formamide and 0.5 μl GeneScan 500LIZ size standard (Applied Biosystems, Foster City, Calif.). The amplified products were separated using an ABI PRISM 3100 Genetic Analyzer (Applied Biosystems). Results were analyzed using GeneScan Analysis software 3.7. Genotyping was performed through comparison with DNA control reference sample 9947A (PowerPlex Y System, Promega, Madison, Wis.), previously typed. The homozygous samples for both markers GATA172D05 and GATA31E08 were also sequenced using ABI 3730 sequencer.

Sample Preparation for Pyrosequencing

Single stranded DNA template was prepared for each sample subjected to pyrosequencing. The 50 μl of biotinylated PCR product was immobilized onto streptavidin-coated super paramagnetic beads (Dynabeads M-280-streptavidin; Dynal AS, Oslo, Norway) by incubation at 42° C. for 10 min. The immobilized PCR product was treated with 50 μl of 20 mM NaOH for 5 minutes to get single stranded DNA. The beads with single stranded DNA were washed one time with 1× annealing buffer (0.1 M Tris-acetate pH 7.75, 200 mM magnesium acetate). The immobilized single stranded DNA was resuspended in to 20 μl of 1× annealing buffer along with 0.5 μM of sequencing primer for each marker. 1 μM PNA oligonucleotide for GATA172D05 and 0.25 μM PNA for each HPRTB and GATA31E08 were also mixed at this step as a polymerization blocking probe. The sequencing primer and PNA were annealed to single stranded template at 50° C. for 5 minutes after 72° C. for 1 minute. The excess sequencing primer and PNA was washed after annealing step before running on pyrosequencer.

Example 3

Combinatorial Pyrosequencing

The Pyrosequencing reaction was performed at 28° C. in 40 µl of reaction volume using an automated PSQ 96 system (Biotage, Uppsala, Sweden). The final volume of 40 µl contained primed target DNA, 30 µl of 1× annealing buffer (0.1 M Tris-acetate pH 7.75, 200 mM magnesium acetate), 5 µl of standard Enzyme mix and 5 µl of standard substrate mix provided by Biotage (www.biotage.com). The dGTP and dATPαS were mixed in equal volume to dispense together allowing polymerase to add two nucleotides at a time during sequencing. Likewise dTTP and dATPαS were also mixed in equal volume to dispense together to interrogate next two bases in template sequence using combinatorial approach. The terminating nucleotide (ddCTP) was purchased from USB Corporation (Cleveland, Ohio, USA) and used in the Pyrosequencing reaction.

In the combinatorial pyrosequencing approach, we dispensed two nucleotides at once to incorporate two bases at a time as a repeat pattern for the known markers under investigation. As a result, we obtained a single peak with a two fold Relative Fluorescence Unit (RFU) which denoted two bases. Because we combined two nucleotides and dispensed them together, this approach is referred to as combinatorial pyrosequencing. This sequencing process continues until it reaches the flanking region of the shortest allele in the heterozygous sample.

Figure 1A:
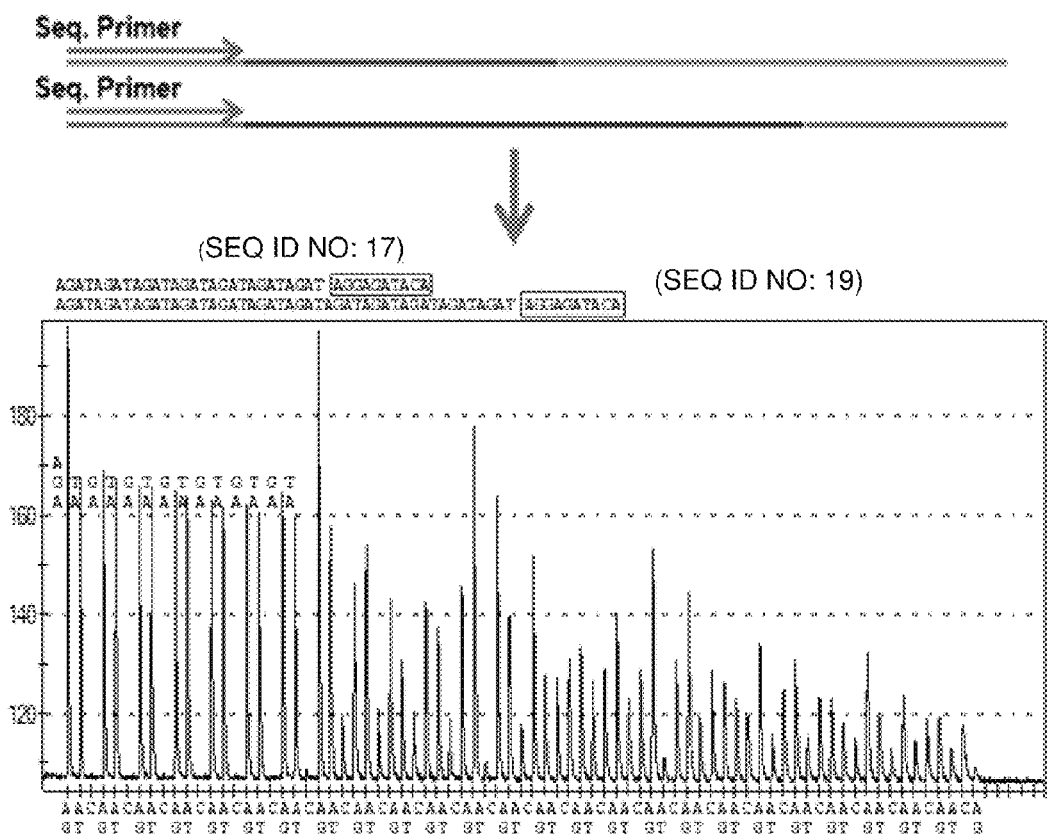
FIGS. 1A-C are further illustrations indicating a heterozygous state in which STRs of different lengths are being analyzed. The bottom row shows the addition of nucleotides, that is, A/G, then A/T, then C, then repeating. The peaks are the signal resulting from incorporation; the top rows show the sequences obtained.
Figure 1B:
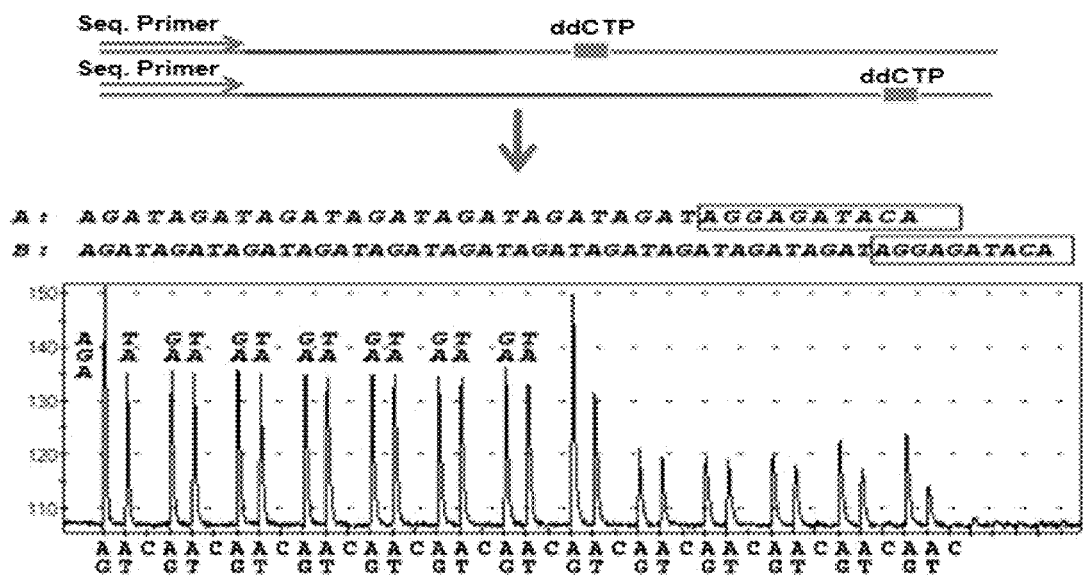
Figure 1C:
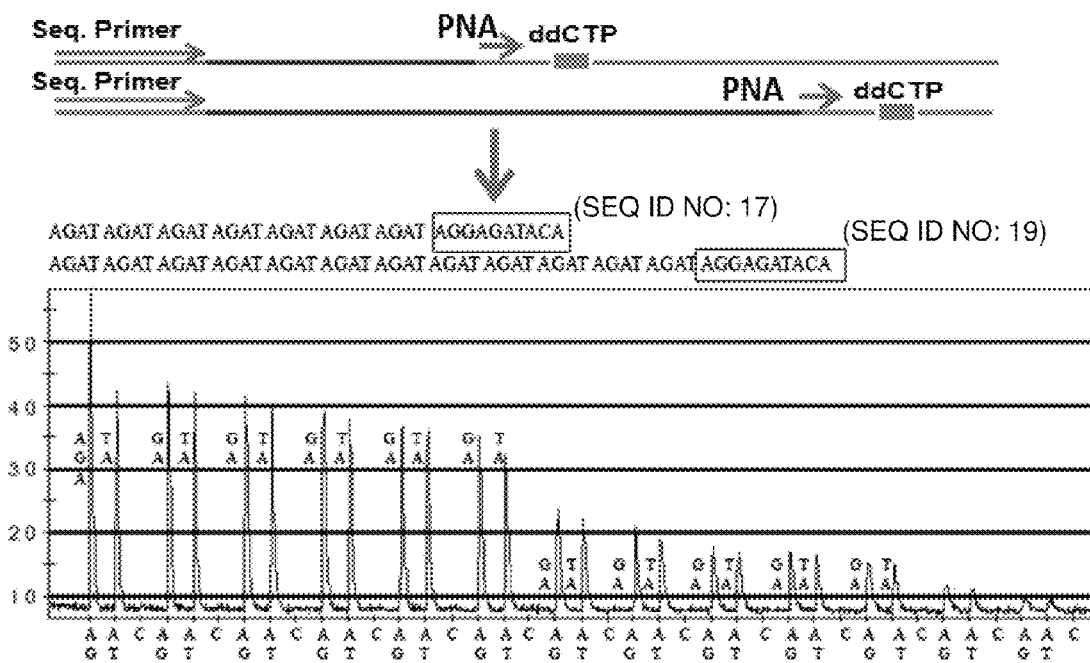

Normally, heterozygous samples cannot be analyzed by pyrosequencing. The unsynchronized polymerization in alleles with different lengths results in no interpretable sequences (depicted in FIG. 1A). However, the selected nucleotide which is not included in the repeat region of markers can be used as a terminating nucleotide to stop polymerization on the shortest allele. Note that the repeat region sequence is TAGA or AGAT for markers included in the examples and ddCTP is used as terminating nucleotide. The terminating nucleotide could be used for template tailoring of those markers which have similar bases in repeat regions. Therefore, common nucleotides can be used as the terminating nucleotide during pyrosequencing. Usually, for specific markers, if the terminating nucleotide is incorporated a few bases away from start point of the flanking region, it results in confusion when assigning genotypes to heterozygous samples (FIG. 1B). Note that incorporation of ddCTP for marker GATA31E08 is at the $9^{th}$ nucleotide as shown in the sequence and results in the wrong genotyping. The bases from flanking region of the shortest allele until the incorporation of ddCTP interferes with repeat regions of the longest allele in pyrosequencing (FIG. 1B). Therefore, PNA was used for first time for DNA template tailoring to sequence the heterozygous samples. In contrast to previous methods, PNA along with the common terminating nucleotide (ddCTP) gave us reliable results (FIG. 1C).

Example 4

Use of Modified Nucleotides

We used PNA complementary to the flanking region as a blocking probe for polymerase. This stops the polymerization on the shortest allele but polymerase processivity continues on to the longest allele in the heterozygous genotype. It results in a reduction of signal by half as polymerization is continued for the longer allele on half the number of copies of the PCR product. By implementing this strategy, we were able to use one common terminating nucleotide (ddCTP) for both markers (GATA172D05 and GATA31E08) along with PNA to establish that we could sequence many markers together in one sequencing run. Therefore, with this approach, flanking region signals do not interfere and resulting genotypes and thus were interpretable as previously reported for autosomal STRs. The Klenow fragment of polymerase has displacement activity for DNA oligonucleotide but it stops polymerization when it reaches the flanking region in our case, because it cannot displace the PNA due to stronger hybridization kinetics. As a result, we are able to do real time DNA length measurement for both homozygous and heterozygous samples in rapid manner.

Example 5

Demonstration of Feasibility of STR Tailoring

The present methods were tested for their ability to measure DNA length of two X-chromosome based STRs, GATA172D05 and GATA31E08, to demonstrate its feasibility. For these studies, the DNA length was determined in 15 DNA samples (9 homozygous and 6 heterozygous samples) for the marker GATA172D05 and 15 DNA samples (7 homozygous and 8 heterozygous samples) for the marker GATA31E08.

Figure 2A:
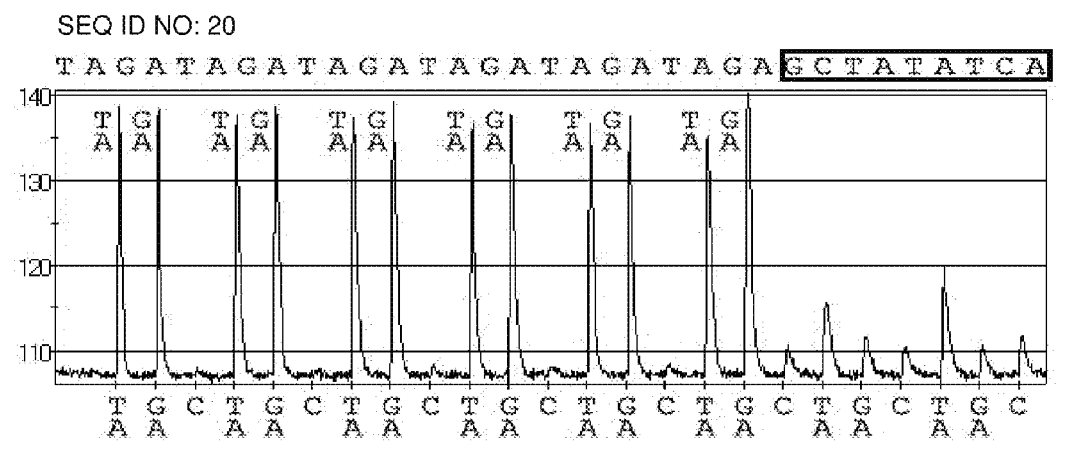
Figure 2B:
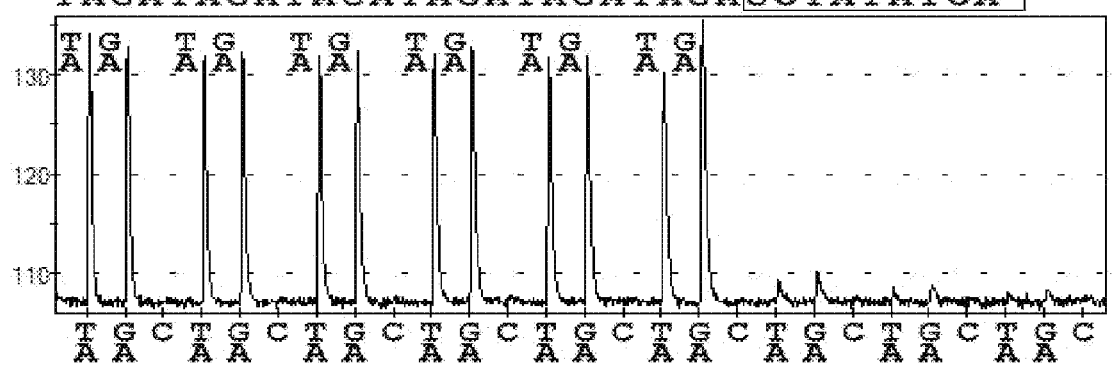
FIG. 2B) Template tailoring of homozygous samples using PNA & ddCTP (genotype 6, 6), FIG. 2C) Template tailoring of heterozygous sample using PNA (genotype 6, 12), FIG. 2D) Template tailoring of heterozygous samples using PNA & ddCTP (genotype 6, 12)
Figure 2C:
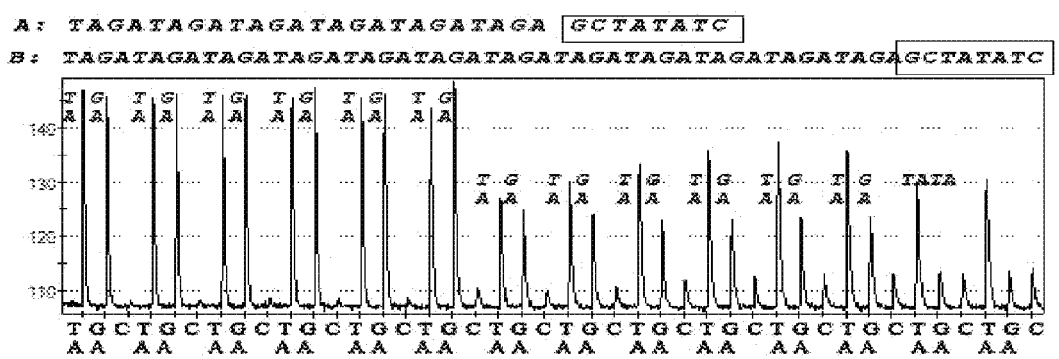
FIGS. 2A, B, C and D show DNA template tailoring by using PNA and ddCTP for homozygous and heterozygous samples for the marker GATA172D05.
Figure 2D:
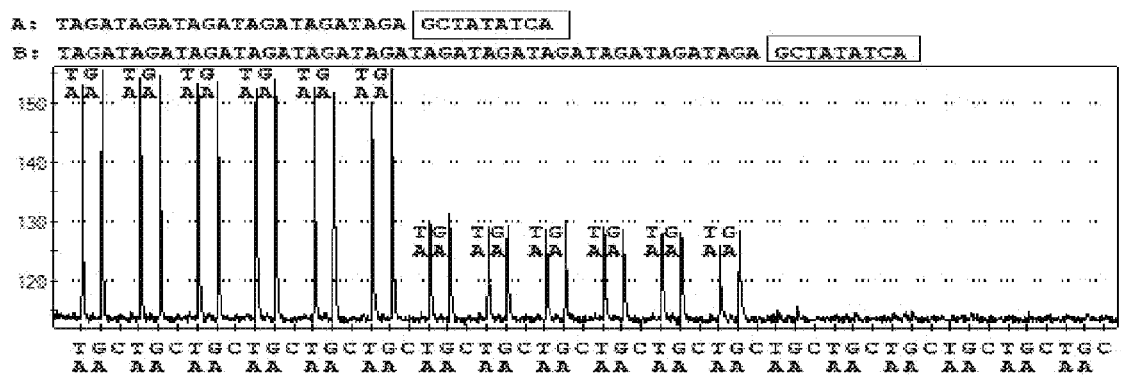

Using only PNA, it was possible to reduce signals for the flanking region and also incorporation of a terminating nucleotide (ddCTP) during the sequencing to further improve the outcome of the runs. PNA alone and PNA as well as ddCTP together for the marker GATA172D05 were used to generate pyrograms shown in FIG. 2. The DNA length for the marker GATA172D05 of homozygous individual samples was measured using only PNA as a blocking probe for polymerase (FIG. 2A). Note that the dispensation order of nucleotides is shown on the bottom of the figure, while output sequences are written along with each peak (each peak represents two bases) and the full sequence of the marker is shown on the top of figure (for heterozygous samples; A, represents the sequence of shortest allele and B, represents the sequence of the longest allele) in each pyrogram shown in the section. The combined effect of PNA and terminating nucleotide for marker GATA172D05 of the homozygous sample is shown in FIG. 2B. The challenging heterozygous sample of marker GATA172D05 was sequenced and a genotype was assigned by using only PNA (FIG. 2C). The combined effect of both PNA and ddCTP for heterozygous samples of marker GATA172 are shown in FIG. 2D.

The PNA concentration from 0.5 µM to 1 µM is suitable for this marker but a significant decrease in signal was found at 1 µM PNA. We did not observe the effect of higher concentrations of PNA, in comparison to the concentrations of PCR product, on the polymerase stacking behavior with respect to this marker, likewise for markers HPRTB and GATA31E08. No signal was detected in the flanking regions except for the first base "G" which increases peak height about 20% of the last peak of the repeat region as shown in FIG. 2.

Figure 3A:
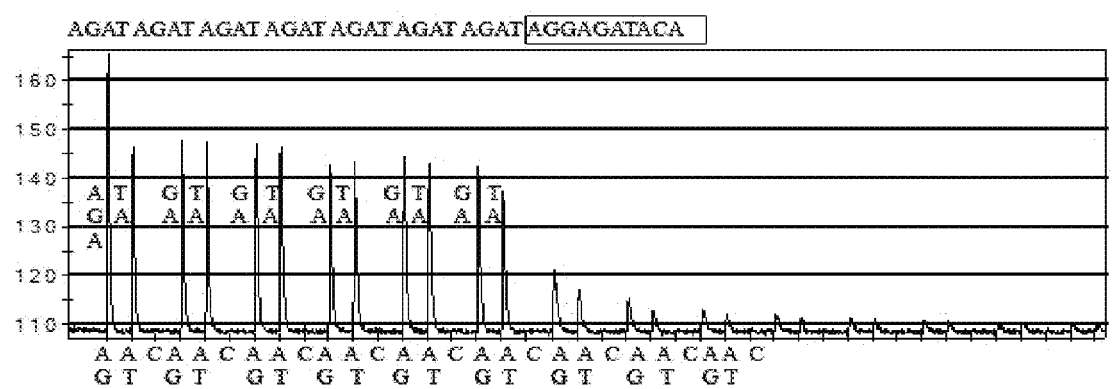
FIGS. 3A and 3B: DNA template tailoring using PNA and ddCTP for homozygous and heterozygous samples for the marker GATA31E08.
Figure 3B:
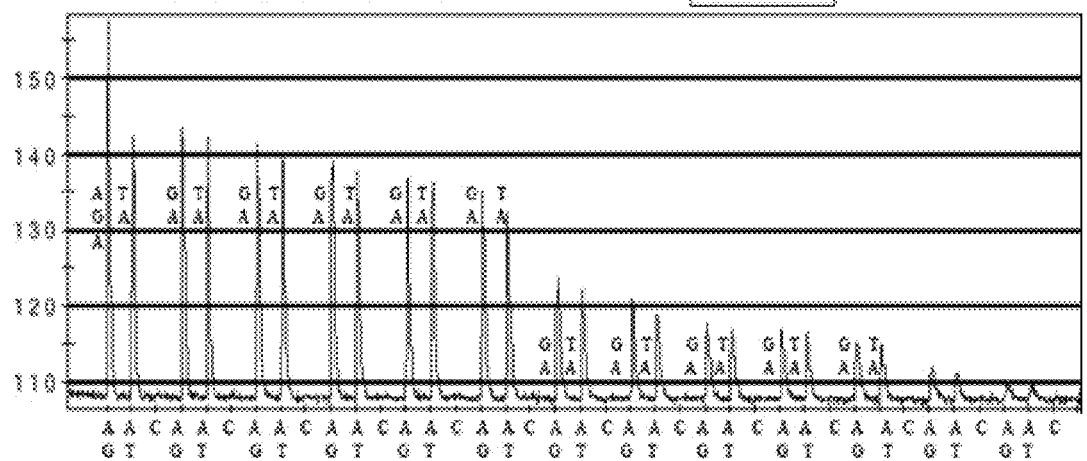

For marker GATA31E08, the PNA oligonucleotide was 4-bp inside the repeat region to check whether Klenow may be able to remove 4 bases as previously reported. The Klenow behaved in the same way for this marker as with GATA172D05 but 0.25 µM PNA is enough to block the polymerase for this marker. The Klenow was not able to remove 4 bases of repeat region. The signal reduction was 67% on the average for sequence having annealed PNA due to strong hybridization kinetics of PNA. The challenging heterozygous sample of marker GATAE08 was sequenced and the genotype was assigned accurately by using ddCTP and PNA. The pyrograms of homozygous and heterozygous individual for marker GATA31E08 are shown in FIG. 3. We also used SYBR green in the reaction to further reduce signals of the flanking regions but it did not show any significant effect. We added one extra repeat to the genotype obtained by pyrosequencing to show the accurate genotypes for each homozygous or heterozygous sample due to the fact that PNA was covering one repeat.

Example 6

Genotype Results

The genotypes of GATA31E08 and GATA172D05 for all samples are shown in Table 3. For marker HPRTB, the PNA oligonucleotide was C-terminus to N-terminus, C-terminus was facing the polymerase enzyme, to check the effect of the 5' functional group on enzyme processivity. It reduced the signals for the flanking region sequences but results were not interpretable. We were not able to differentiate between homozygous and heterozygous samples. We concluded that the N-terminus of PNA facing polymerase, N-terminus to C-terminus PNA, appeared to be the best blocking probe for DNA length measurement using pyrosequencing. The data for genotypes of HPRTB are not included due to unreliability. The genotypes assigned to samples by the present method employing combinatorial pyrosequencing were concordant with genotypes obtained by genetic analyzer and Sanger sequencing for all samples including both markers GATA172D05 and GATA31E08.

TABLE 3

| Sample | GATA172D05 | Sample | GATA31E08 |
|---|---|---|---|
| 01 | 6, 6 | 01 | 13, 13 |
| 02 | 10, 10 | 02 | 11, 11 |
| 03 | 10, 10 | 03 | 7, 7 |
| 04 | 8, 10 | 06 | 9, 9 |
| 06 | 10, 10 | 08 | 11, 11 |
| 08 | 12, 12 | 09 | 12, 12 |
| 09 | 11, 11 | Ak3 | 10, 13 |
| 10 | 6, 9 | Ak5 | 9, 12 |
| Ak2 | 6, 12 | Ak6 | 9, 12 |
| Ak4 | 8, 8 | Ak8 | 9, 12 |
| Ak5 | 10, 12 | Ak9 | 10, 10 |
| Ak8 | 11, 12 | Ak11 | 7, 12 |
| Ak9 | 10, 12 | Ak12 | 7, 7 |
| Ak10 | 11, 11 | Ak13 | 7, 11 |
| Ak15 | 8, 8 | Ak19 | 11, 12 |

Genotypes produced by combinatorial pyrosequencing were confirmed by the genetic analyzer ABI3100 and results were the same.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method for characterizing by length of a repetitive sequence in a sample nucleic acid, said repetitive sequence having a location between a 5' flanking region and a 3' flanking region, the method comprising the steps of:
   (a) hybridizing a polymerization primer to said 3' flanking region;
   (b) hybridizing a modified oligonucleotide to said 5' flanking region, said modified oligonucleotide being resistant to displacement by a polymerase enzyme;
   (c) extending the polymerization primer in a 5' to 3' direction by using said polymerase enzyme, said extending stopping at 5' end of the modified oligonucleotide; and
   (d) said extending comprising the step of adding nucleotides complementary to the sample sequence and the step of adding a dideoxy nucleotide selected to be only complementary to a nucleotide in the 5' flanking region, whereby extending proceeds from said polymerization primer to the modified oligonucleotide unless terminated by an added dideoxynucleotide,
   wherein the repetitive sequence is characterized by length of extending in step (c) and (d).

2. The method of claim 1 wherein the sample nucleic acid repetitive sequence comprises short tandem repeats (STRs) in a genomic sample.

3. The method of claim 2 wherein the modified oligonucleotide is a peptide nucleic acid.

4. The method of claim 2 where the STRs are selected from the group consisting of: CSF1PO, D3S1358, D5S818, D7S820, D8S1179, D13S317, D16S539, D18S51, D21S11, FGA, TH01, TPDX, and VWA.

5. The method of claim 1 where the sample nucleic acid sequence comprises a feature selected from the group consisting of a short tandem repeat region, a variable number tandem repeat region, and a microsatellite region.

6. The method of claim 5 wherein the modified oligonucleotide is a peptide nucleic acid.

7. The method of claim 1 wherein the modified oligonucleotide is a peptide nucleic acid.

8. The method of claim 7 where the peptide nucleic acid is hybridized with an N terminus at the 3' end of the flanking region.

9. The method of claim 1 wherein the extending comprises determining a sequence between said 5' flanking region and said 3' flanking region using a sequencing-by-synthesis method.

10. The method of claim 9 wherein nucleotides are added two at a time.

11. The method of claim 9 where the extending is done by a pyrosequencing method.

12. A method for characterizing a sample sequence by length, said length being related to a number of tandem repeats, said tandem repeats being located between a 5' flanking region and a 3' flanking region, the method comprising the steps of:
   (a) hybridizing a polymerization primer to said 3' flanking region of the tandem repeats;
   (b) hybridizing a blocking probe to said 5' flanking region of the tandem repeats, said blocking probe being resistant to displacement by a polymerase enzyme;
   (c) extending the polymerization primer in a 5' to 3' direction by using said polymerase enzyme, said extending stopping at 5' end of the blocking probe; and
   (d) said extending comprising the step of adding nucleotides complementary to the sample sequence and adding a dideoxy nucleotide only complementary to a nucleotide in the 5' flanking, whereby extending proceeds from said polymerization primer to the modified oligonucleotide unless terminated by a dideoxynucleotide,
   wherein a tandem repeat sequence length is characterized by length of extending in step (c) and (d).

* * * * *

UNITED STATES PATENT AND TRADEMARK OFFICE
CERTIFICATE OF CORRECTION

PATENT NO.         : 9,187,782 B2                                    Page 1 of 1
APPLICATION NO.    : 13/027926
DATED              : November 17, 2015
INVENTOR(S)        : Pourmand et al.

It is certified that error appears in the above-identified patent and that said Letters Patent is hereby corrected as shown below:

IN THE CLAIMS:

Column 31, line 39 (Claim 4, line 4) delete "TPDX" and insert --TPOX--.

Signed and Sealed this
Twenty-sixth Day of July, 2016

Michelle K. Lee
*Director of the United States Patent and Trademark Office*

SEQUENCE LISTING

<160> NUMBER OF SEQ ID NOS: 51

<210> SEQ ID NO 1
<211> LENGTH: 20
<212> TYPE: DNA
<213> ORGANISM: Human

<400> SEQUENCE: 1
tagtggtgat ggttgcacag                                               20

<210> SEQ ID NO 2
<211> LENGTH: 20
<212> TYPE: DNA
<213> ORGANISM: Human

<400> SEQUENCE: 2
ataattgaaa gcccggattc                                               20

<210> SEQ ID NO 3
<211> LENGTH: 20
<212> TYPE: DNA
<213> ORGANISM: Human

<400> SEQUENCE: 3 agggagaag gctagaatga                                                20

```
<210> SEQ ID NO 4
<211> LENGTH: 20
<212> TYPE: DNA
<213> ORGANISM: Human

<400> SEQUENCE: 4
cagctgacag agcacagaga                                              20

<210> SEQ ID NO 5
<211> LENGTH: 20
<212> TYPE: DNA
<213> ORGANISM: Human

<400> SEQUENCE: 5
ataattgaaa gcccggattc                                              20

<210> SEQ ID NO 6
<211> LENGTH: 20
<212> TYPE: DNA
<213> ORGANISM: Human

<400> SEQUENCE: 6
tagtggtgat ggttgcacag                                              20

<210> SEQ ID NO 7
<211> LENGTH: 20
<212> TYPE: DNA
<213> ORGANISM: Human

<400> SEQUENCE: 7
gtgatggttg cacagatata                                              20

<210> SEQ ID NO 8
<211> LENGTH: 15
<212> TYPE: DNA
<213> ORGANISM: Human

<400> SEQUENCE: 8
gctatatcaa tacct                                                   15

<210> SEQ ID NO 9
<211> LENGTH: 20
<212> TYPE: DNA
<213> ORGANISM: Human

<400> SEQUENCE: 9
cagctgacag agcacagaga                                              20

<210> SEQ ID NO 10
<211> LENGTH: 20
<212> TYPE: DNA
<213> ORGANISM: Human

<400> SEQUENCE: 10
aggggagaag gctagaatga                                              20

<210> SEQ ID NO 11
<211> LENGTH: 19
<212> TYPE: DNA
<213> ORGANISM: Human

<400> SEQUENCE: 11
agatagatga tagggaggg                                               19
```

```
<210> SEQ ID NO 12
<211> LENGTH: 15
<212> TYPE: DNA
<213> ORGANISM: Human

<400> SEQUENCE: 12
agataggaga tacat                                                    15

<210> SEQ ID NO 13
<211> LENGTH: 24
<212> TYPE: DNA
<213> ORGANISM: Human

<400> SEQUENCE: 13
gtctctattt ccatctctgt ctcc                                          24

<210> SEQ ID NO 14
<211> LENGTH: 21
<212> TYPE: DNA
<213> ORGANISM: Human

<400> SEQUENCE: 14
ttctttctct cacccctgtc t                                             21

<210> SEQ ID NO 15
<211> LENGTH: 21
<212> TYPE: DNA
<213> ORGANISM: Human

<400> SEQUENCE: 15
gagaagggca tgaatttgct t                                             21

<210> SEQ ID NO 16
<211> LENGTH: 15
<212> TYPE: DNA
<213> ORGANISM: Human

<400> SEQUENCE: 16
gatagacaga tagag                                                    15

<210> SEQ ID NO 17
<211> LENGTH: 38
<212> TYPE: DNA
<213> ORGANISM: Human

<400> SEQUENCE: 17
agatagatag atagatagat agatagatag gagataca                           38

<210> SEQ ID NO 18
<211> LENGTH: 54
<212> TYPE: DNA
<213> ORGANISM: Human

<400> SEQUENCE: 18
agatagatag atagatagat agatagatag atagatagat agataggaga taca         54

<210> SEQ ID NO 19
<211> LENGTH: 58
<212> TYPE: DNA
<213> ORGANISM: Human

<400> SEQUENCE: 19
agatagatag atagatagat agatagatag atagatagat agatagatag gagataca    58
```

<210> SEQ ID NO 20
<211> LENGTH: 33
<212> TYPE: DNA
<213> ORGANISM: Human

<400> SEQUENCE: 20
tagatagata gatagataga tagagctata tca                         33

<210> SEQ ID NO 21
<211> LENGTH: 32
<212> TYPE: DNA
<213> ORGANISM: Human

<400> SEQUENCE: 21
tagatagata gatagataga tagagctata tc                          32

<210> SEQ ID NO 22
<211> LENGTH: 56
<212> TYPE: DNA
<213> ORGANISM: Human

<400> SEQUENCE: 22
tagatagata gatagataga tagatagata gatagataga tagatagagc tatatc    56

<210> SEQ ID NO 23
<211> LENGTH: 57
<212> TYPE: DNA
<213> ORGANISM: Human

<400> SEQUENCE: 23
tagatagata gatagataga tagatagata gatagataga tagatagagc tatatca   57

<210> SEQ ID NO 24
<211> LENGTH: 23
<212> TYPE: DNA
<213> ORGANISM: Human

<400> SEQUENCE: 24
tctctatttc catctctgtc tcc                                    23

<210> SEQ ID NO 25
<211> LENGTH: 21
<212> TYPE: DNA
<213> ORGANISM: Human

<400> SEQUENCE: 25
tcacccctgt ctatggtctc g                                      21

<210> SEQ ID NO 26
<211> LENGTH: 24
<212> TYPE: DNA
<213> ORGANISM: Human

<400> SEQUENCE: 26
aacctgagtc tgccaaggac tagc                                   24

<210> SEQ ID NO 27
<211> LENGTH: 24
<212> TYPE: DNA
<213> ORGANISM: Human

<400> SEQUENCE: 27

-continued ttccacacac cactggccat cttc     24

<210> SEQ ID NO 28
<211> LENGTH: 21
<212> TYPE: DNA
<213> ORGANISM: Human

<400> SEQUENCE: 28
gccccatagg ttttgaactc a     21

<210> SEQ ID NO 29
<211> LENGTH: 22
<212> TYPE: DNA
<213> ORGANISM: Human

<400> SEQUENCE: 29
tgatttgtct gtaattgcca gc     22

<210> SEQ ID NO 30
<211> LENGTH: 24
<212> TYPE: DNA
<213> ORGANISM: Human

<400> SEQUENCE: 30
gtgggctgaa aagctcccga ttat     24

<210> SEQ ID NO 31
<211> LENGTH: 24
<212> TYPE: DNA
<213> ORGANISM: Human

<400> SEQUENCE: 31
attcaaaggg tatctgggct ctgg     24

<210> SEQ ID NO 32
<211> LENGTH: 24
<212> TYPE: DNA
<213> ORGANISM: Human

<400> SEQUENCE: 32
actggcacag aacaggcact tagg     24

<210> SEQ ID NO 33
<211> LENGTH: 24
<212> TYPE: DNA
<213> ORGANISM: Human

<400> SEQUENCE: 33
ggaggaactg ggaaccacac aggt     24

<210> SEQ ID NO 34
<211> LENGTH: 21
<212> TYPE: DNA
<213> ORGANISM: Human

<400> SEQUENCE: 34
ccctagtgga taagaataat c     21

<210> SEQ ID NO 35
<211> LENGTH: 30
<212> TYPE: DNA
<213> ORGANISM: Human

<400> SEQUENCE: 35

```
ggacagatga taaatacata ggatggatgg                                      30

<210> SEQ ID NO 36
<211> LENGTH: 19
<212> TYPE: DNA
<213> ORGANISM: Human

<400> SEQUENCE: 36
actgcagtcc aatctgggt                                                  19

<210> SEQ ID NO 37
<211> LENGTH: 20
<212> TYPE: DNA
<213> ORGANISM: Human

<400> SEQUENCE: 37
atgaaatcaa cagaggcttg                                                 20

<210> SEQ ID NO 38
<211> LENGTH: 23
<212> TYPE: DNA
<213> ORGANISM: Human

<400> SEQUENCE: 38
ggtgattttc ctctttggta tcc                                             23

<210> SEQ ID NO 39
<211> LENGTH: 26
<212> TYPE: DNA
<213> ORGANISM: Human

<400> SEQUENCE: 39
agccacagtt tacaacattt gtatct                                          26

<210> SEQ ID NO 40
<211> LENGTH: 21
<212> TYPE: DNA
<213> ORGANISM: Human

<400> SEQUENCE: 40
atgttggtca ggctgactat g                                               21

<210> SEQ ID NO 41
<211> LENGTH: 24
<212> TYPE: DNA
<213> ORGANISM: Human

<400> SEQUENCE: 41
gattccacat ttatcctcat tgac                                            24

<210> SEQ ID NO 42
<211> LENGTH: 25
<212> TYPE: DNA
<213> ORGANISM: Human

<400> SEQUENCE: 42
tttttgtatt tcatgtgtac attcg                                           25

<210> SEQ ID NO 43
<211> LENGTH: 25
<212> TYPE: DNA
<213> ORGANISM: Human
```

```
<400> SEQUENCE: 43
cgtagctata attagttcat tttca                                          25

<210> SEQ ID NO 44
<211> LENGTH: 26
<212> TYPE: DNA
<213> ORGANISM: Human

<400> SEQUENCE: 44
attacagaag tctgggatgt ggagga                                         26

<210> SEQ ID NO 45
<211> LENGTH: 19
<212> TYPE: DNA
<213> ORGANISM: Human

<400> SEQUENCE: 45
ggcagcccaa aaagacaga                                                 19

<210> SEQ ID NO 46
<211> LENGTH: 24
<212> TYPE: DNA
<213> ORGANISM: Human

<400> SEQUENCE: 46
gggggtctaa gagcttgtaa aaag                                           24

<210> SEQ ID NO 47
<211> LENGTH: 29
<212> TYPE: DNA
<213> ORGANISM: Human

<400> SEQUENCE: 47
gtttgtgtgt gcatctgtaa gcatgtatc                                      29

<210> SEQ ID NO 48
<211> LENGTH: 20
<212> TYPE: DNA
<213> ORGANISM: Human

<400> SEQUENCE: 48
caaacccgac taccagcaac                                                20

<210> SEQ ID NO 49
<211> LENGTH: 20
<212> TYPE: DNA
<213> ORGANISM: Human

<400> SEQUENCE: 49
gagccatgtt catgccactg                                                20

<210> SEQ ID NO 50
<211> LENGTH: 18
<212> TYPE: DNA
<213> ORGANISM: Human

<400> SEQUENCE: 50
gtgagtcaat tccccaag                                                  18

<210> SEQ ID NO 51
<211> LENGTH: 22
<212> TYPE: DNA
<213> ORGANISM: Human
```

```
<400> SEQUENCE: 51
gttgtattag tcaatgttct cc                                                    22
```